(12) United States Patent
Asthana et al.

(10) Patent No.: US 11,631,497 B2
(45) Date of Patent: Apr. 18, 2023

(54) PERSONALIZED DEVICE RECOMMENDATIONS FOR PROACTIVE HEALTH MONITORING AND MANAGEMENT

(71) Applicant: International Business Machines Corporation, Armonk, NY (US)

(72) Inventors: Shubhi Asthana, Santa Clara, CA (US); Aly Megahed, San Jose, CA (US); Hovey R. Strong, Jr., San Jose, CA (US); Samir Tata, Cupertino, CA (US)

(73) Assignee: International Business Machines Corporation, Armonk, NY (US)

( * ) Notice: Subject to any disclaimer, the term of this patent is extended or adjusted under 35 U.S.C. 154(b) by 618 days.

(21) Appl. No.: 15/993,381

(22) Filed: May 30, 2018

(65) Prior Publication Data
US 2019/0371463 A1    Dec. 5, 2019

(51) Int. Cl.
*G16H 50/20*       (2018.01)
*G16H 50/30*       (2018.01)
*G06N 20/00*       (2019.01)

(52) U.S. Cl.
CPC ............. *G16H 50/20* (2018.01); *G06N 20/00* (2019.01); *G16H 50/30* (2018.01)

(58) Field of Classification Search
CPC ........ G16H 50/20; G16H 50/30; G16H 40/20; G16H 50/70; G16H 10/60; G06N 20/00; G06N 5/003; G06N 7/005; G06K 9/6267
See application file for complete search history.

(56) References Cited

U.S. PATENT DOCUMENTS 7,542,947 B2    6/2009  Guyon et al.
8,145,590 B2    3/2012  Brockway et al.
(Continued)

FOREIGN PATENT DOCUMENTS

CN    105235215 A    1/2016
WO    2016151445 A1   9/2016
(Continued)

OTHER PUBLICATIONS

International Search Report and Written Opinion from PCT Application No. PCT/IB2019/053917, dated Aug. 20, 2019.
(Continued)

*Primary Examiner* — Mark Holcomb
*Assistant Examiner* — Chad A Newton
(74) *Attorney, Agent, or Firm* — Zilka-Kotab, P.C.

(57) ABSTRACT

Systems, methods, and computer program products for providing personalized recommendations of devices for monitoring and/or managing a health condition are disclosed, and generally include receiving first structured information regarding a patient and a first set of one or more patient populations; receiving unstructured information regarding at least the patient and a second set of one or more patient populations; analyzing the unstructured information to derive second structured information; determining one or more health metrics to be monitored for the patient based on analyzing each of the first structured information and the second structured information, using a classification model; and determining an optimum set of devices to be used for monitoring the one or more health metrics. In some embodiments, metrics may be continuously monitored to detect a change exceeding an event trigger threshold, and a new set of recommended devices may be generated.

16 Claims, 5 Drawing Sheets

(56) References Cited

U.S. PATENT DOCUMENTS

| | | | |
|---|---|---|---|
| 8,684,922 | B2 | 4/2014 | Tran |
| 8,714,983 | B2 | 5/2014 | Kil |
| 8,930,212 | B2 | 1/2015 | Oakley et al. |
| 9,107,586 | B2 | 8/2015 | Tran |
| 9,215,980 | B2 | 12/2015 | Tran et al. |
| 9,262,772 | B2 | 2/2016 | Stivoric et al. |
| 9,307,944 | B2 | 4/2016 | Colman et al. |
| 9,536,052 | B2 | 1/2017 | Amarasingham et al. |
| 2010/0161236 | A1 | 6/2010 | Cohen et al. |
| 2010/0223215 | A1* | 9/2010 | Karypis ............... G06Q 10/04 706/12 |
| 2012/0165617 | A1 | 6/2012 | Vesto et al. |
| 2014/0107932 | A1 | 4/2014 | Luna |
| 2014/0288950 | A1 | 9/2014 | Park et al. |
| 2015/0019342 | A1 | 1/2015 | Gupta |
| 2015/0269825 | A1 | 9/2015 | Tran |
| 2016/0098539 | A1 | 4/2016 | Zamanakos et al. |
| 2016/0179962 | A1 | 6/2016 | Patten et al. |
| 2016/0224750 | A1 | 8/2016 | Kethman et al. |
| 2016/0283671 | A1* | 9/2016 | Bhaskar ............... G16H 50/20 |
| 2016/0371457 | A1 | 12/2016 | Zillner |
| 2018/0005126 | A1* | 1/2018 | Yamagami et al. ..... G06N 5/04 |
| 2018/0068083 | A1* | 3/2018 | Cohen .................... G16H 10/60 |
| 2018/0113982 | A1 | 4/2018 | Asthana et al. |
| 2018/0189163 | A1* | 7/2018 | Megahed ............ G06F 11/3006 |
| 2019/0216350 | A1* | 7/2019 | Sullivan ............... A61N 1/0484 |
| 2020/0121851 | A1* | 4/2020 | Rinehart ........... A61M 5/16877 |

FOREIGN PATENT DOCUMENTS

| | | |
|---|---|---|
| WO | 2016176219 A1 | 11/2016 |
| WO | 2018084166 A1 | 5/2018 |

OTHER PUBLICATIONS

Davis et al., "Predicting Individual Disease Risk Based on Medical History," Proceedings of the 17th ACM Conference on Information and Knowledge Management, 2008, pp. 769-778.

Danova, T., "The Wearable Computing Market Report: Growth Trends, Consumer Attitudes, And Why Smartwatches Will Dominate," BI Intelligence, Oct. 29, 2014, pp. 1-29.

Bonato, P., "Wearable Sensors/Systems and Their Impacton Biomedical Engineering," IEEE Engineering in Medicine and Biology Magazine, May/Jun. 2003, pp. 18-20.

USA LifeExpectancy, "USA Causes of Death by Age and Gender," Dec. 2017, 3 pages retrieved from http://www.worldlifeexpectancy.com/usa-cause-of-death-by-age-and-gender.

Janssens et al., "Genome-based prediction of common diseases: advances and prospects," Human Molecular Genetics, vol. 17, No. 2, 2008, pp R166-R173.

Wray et al., "Prediction of individual genetic risk to disease from genome-wide association studies," Genome Research, 2007, pp. 1520-1528.

Khalilia et al., "Predicting disease risks from highly imbalanced data using random forest," BMC Medical Informatics & Decision Making, vol. 11, 2011, pp. 1-13.

Mayo Clinic, "Heart Disease Risk Calculator," 2018, 2 pages retrieved from http://www.mayoclinic.org/diseases-conditions/heart-disease/in-depth/heart-disease-risk/itt-20084942.

Spire, "Make Your Clothes Smart," 2018, 5 pages retrieved from https://www.spire.io/.

Weka, "Weka 3: Data Mining Software in Java," 2018, 1 page, retrieved from http://www.cs.waikato.ac.nz/ml/weka/.

Holte, R.C., "Very Simple Classification Rules Perform Well on Most Commonly Used Datasets," Machine Learning, vol. 11, 1993, pp. 63-90.

Vandrico Inc., "The Wearables Database," 2018, pp. 1-6 retrieved from http://vandrico.com/wearables/wearable-technology-database.

McCormick et al., "Bayesian Hierarchical Rule Modeling for Predicting Medical Conditions," The Annals of Applied Statistics, vol. 6, No. 2, 2012, pp. 1-17.

Choi et al., "RETAIN: Interpretable Predictive Model in Healthcare using Reverse Time Attention Mechanism," 29th Conference on Neural Information Processing Systems, 2016, pp. 1-13.

Paxton et al., "Developing Predictive Models Using Electronic Medical Records: Challenges and Pitfalls," Proceedings of the AMIA Annual Symposium, 2013, pp. 1109-1115.

PWC, "Health Wearables: Early Days," PWC Health Research Institute, 2014, 12 pages.

Ukowicz et al., "AMON: A Wearable Medical Computer for High Risk Patients," Proceedings of the 6th International Symposium on Wearable Computers (ISWC'02), 2002, pp. 1-2.

Milenkovic et al., "Wireless sensor networks for personal health monitoring: Issues and an implementation," Computer Communications, vol. 29, 2006, pp. 1-13.

Varshney, U., "Pervasive Healthcare and Wireless Health Monitoring," Mobile Networks and Applications, vol. 12, 2007, pp. 113-127.

Otto et al., "System Architecture of a Wireless Body Area Sensor Network for Ubiquitous Health Monitoring," Journal of Mobile Multimedia, vol. 1, No. 4, 2006, pp. 307-326.

Sung et al., "Wearable feedback systems for rehabilitation," Journal of Neuroengineering and Rehabilitation, vol. 2, No. 17, Jun. 2005, pp. 1-12.

Komninos et al., "HealthPal: An Intelligent Personal Medical Assistant for Supporting the Self-Monitoring of Healthcare in the Ageing Society," Proceedings of the UbiHealth, 2006, 13 pages.

Ramos, J., "Using IF-IDF to Determine Word Relevance in Document Queries," Proceedings of the First Instructional Conference on Machine Learning, 2003, 4 pages.

Hall et al., "The WEKA Data Mining Software: An Update," SIGKDD explorations, vol. 11, No. 1, Jul. 2009, pp. 10-18.

Asthana et al., "HealthAdvisor: Recommendation System for Wearable Technologies enabling Proactive Health Monitoring," arXiv preprint, 2016, pp. 1-5 retrieved from https://arxiv.org/ftp/arxiv/papers/1612/1612.00800.pdf.

Lopez-Meyer et al., "Monitoring of Cigarette Smoking Using Wearable Sensors and Support Vector Machines," IEEE Transactions on Biomedical Engineering, vol. 60, No. 7, Jul. 2013, pp. 1867-1872.

Korhonen et al., "Health Monitoring in the Home of the Future," IEEE Engineering in Medicine and Biology Magazine, May-Jun. 2003, pp. 66-73.

Pantelopoulos et al., "A Survey on Wearable Biosensor Systems for Health Monitoring," 30th Annual International IEEE EMBS Conference, Aug. 2008, pp. 4887-4890.

Tata et al., "An Optimization Approach for Adaptive Monitoring in IoT Environments," IEEE 14th International Conference on Services Computing, 2017, pp. 378-385.

Hastie et al., "The Elements of Statistical Learning," Springer Series in Statistics, 2nd Edition, 2009, 764 pages.

Ashby et al., "Evidence-Based Medicine as Bayesian Decision-Making," Statistics In Medicine, 2000, pp. 1-15.

Spiegelhalter et al., "Statistical and Knowledge-Based Approaches to Clinical Decision-Support Systems, with an Application in Gastroenterology," J. R. Statist. Soc. A, 1984, 147, pp. 35-77.

Jensen, "Introduction to Bayesian Networks," Advanced Hard Management, Sep. 2009, pp. 1-8.

GNS Healthcare, "MAX Architecture," Aug. 6, 2016, pp. 1-5, Retrieved From https://web.archive.org/web/20160806035715/http://www.gnshealthcare.com/technology-overview/technology/.

Krishnamurthy et al., "SystemT: A System for Declarative Information Extraction," SIGMOD Record, vol. 37, No. 4, Dec. 2008, pp. 7-13.

IBM Biginsights on Cloud, "Hadoop-As-A-Service, Big Data Analytics In The Cloud," Apr. 28, 2016, pp. 1, Retrieved From http://www-03.ibm.com/software/products/en/ibm-biginsights-on-cloud.

Mascarenhas, "Willis Towers Watson Develops New Technology To More Accurately Predict When You're Going To Die," International Business Times, Apr. 4, 2016, pp. 1-3, Retrieved From http://www.ibtimes.co.uk/willis-towers-watson-develops-new-technology-more-accurately-predict-when-youre-going-die-1553048.

Examination Report from European Application No. GB2018705.0, dated Mar. 24, 2022.

(56) References Cited

OTHER PUBLICATIONS

Hall et al., "Why are Neural Networks Sometimes Much More Accurate than Decision Trees: An Analysis on a Bio-Informatics Problem," IEEE SMC'03, International Conference on Systems, Man and Cybernetics, 2003, 6 pages.

Caruana et al., "An Empirical Comparison of Supervised Learning Algorithms," Proceedings of the 23rd International Conference on Machine Learning, 2006, 8 pages.

Karakurt et al., "Comparing ensembles of decision trees and neural networks for one-day-ahead streamflow prediction," Scientific Research Journal, vol. 1, No. IV, Nov. 2013, pp. 43-55.

DTREG, "Decision Trees Compared to Regression and Neural Networks," DTREG predictive modeling software, 2022, 2 pages, retrieved from https://www.dtreg.com/methodology/view/decision-trees-cornpared-to-regression-and-neural-networks#:~:text=Neural%20networks%20are%20often%20compared,drawbacks%20compared%20to%20decision%20trees.

Mljar, "Decision Tree vs Neural Network," mjlar, 2022, 47 pages, retrievred from https://mljar.com/machine-leaming/decision-tree-vs-neural-network/.

Decision to Grant a Patent from Japanese Application No. 2020-564171, dated Oct. 4, 2022.

\* cited by examiner

PERSONALIZED DEVICE RECOMMENDATIONS FOR PROACTIVE HEALTH MONITORING AND MANAGEMENT

BACKGROUND

The present invention relates to health care, and more specifically, this invention relates to recommending devices for personalized health care monitoring and management based on patient demographics and medical history (of the individual patient and/or patient populations). The device recommendations are preferably individually tailored to take into account technological and/or financial constraints of the patient and/or operating environment.

Health care is a vitally important aspect of the modern economy and requires using a complex set of information to accurately diagnose patients and recommend appropriate treatment. With the advance of electronic health care records, data-driven health care is an increasing area of interest to health care professionals, and may improve the quality and efficiency with which health care services are provided and patient treatment is accomplished.

In addition, the rising popularity of portable sensors and devices to monitor health conditions provides additional opportunities to observe health status progression with precise metrics. However, currently existing sensors and devices do not provide the ability to monitor all relevant health metrics, and the use of such sensors and devices does not occur to all health care professionals, ultimately leaving a gap between the information needed to improve health care and the ability to collect such information.

Moreover, even if an appropriate sensor/device or combination thereof is available to monitor an individual's health, it may be financially and/or technologically impractical for the particular sensor/device to operate in the desired manner. For instance, a particular patient may not be able to afford one type of sensor/device suitable for monitoring a given health condition, but may be able to afford a different, less expensive type of sensor/device capable of monitoring the given health condition. Similarly, a particular patient may not be present in a network-accessible location for extended periods of time, such that sensors/devices requiring active network connections may not be able to perform adequately. Devices/Sensors and networks may also have inherent limitations, including e.g. processing power, data storage capacity, bandwidth, latency, etc. These financial, technological, and other associated practical considerations/limitations are not typically accounted for in a conventional medical environment/interaction and patients may be required to use inappropriate or suboptimal monitoring technology, denigrating the amount and/or quality of information collected and corresponding treatment outcomes.

Accordingly, it would be advantageous to provide systems and techniques configured to facilitate patient treatment and health care monitoring using a data-driven approach that considers medical information, demographics, and practical considerations, to recommend appropriate sensors and devices for monitoring and managing health conditions.

SUMMARY

In one embodiment, a computer program product for providing personalized recommendations of devices for monitoring and/or managing a health condition includes a computer readable storage medium having program instructions embodied therewith, where the computer readable storage medium is not a transitory signal per se. The program instructions are executable by a processor to cause the processor to perform a method including: receiving, at the processor, first structured information regarding a patient and a first set of one or more patient populations; receiving, at the processor, unstructured information regarding at least the patient and a second set of one or more patient populations; analyzing, by the processor, the unstructured information to derive second structured information; determining, by the processor one or more health metrics to be monitored for the patient based on analyzing the first structured information and the second structured information using a classification model; and determining, by the processor, an optimum set of devices to be used for monitoring the one or more health metrics.

In accordance with another embodiment, a computer-implemented method for providing personalized recommendations of devices for monitoring and/or managing a health condition includes: receiving first structured information regarding a patient and a first set of one or more patient populations; receiving unstructured information regarding at least the patient and a second set of one or more patient populations; analyzing the unstructured information to derive second structured information; determining one or more health metrics to be monitored for the patient based on analyzing the first structured information and the second structured information using a classification model; and determining an optimum set of devices to be used for monitoring the one or more health metrics.

In yet another embodiment, a system for providing personalized recommendations of devices for monitoring and/or managing a health condition includes a processor and logic in and/or executable by the processor to cause the processor to: receive first structured information regarding a patient and a first set of one or more patient populations; receive unstructured information regarding at least the patient and a second set of one or more patient populations; analyzing the unstructured information to derive second structured information; determine one or more health metrics to be monitored for the patient based on analyzing the first structured information and the second structured information using a classification model; and determine an optimum set of devices to be used for monitoring the one or more health metrics.

Other aspects and embodiments of the present invention will become apparent from the following detailed description, which, when taken in conjunction with the drawings, illustrate by way of example the principles of the invention.

DETAILED DESCRIPTION

Figure 1:
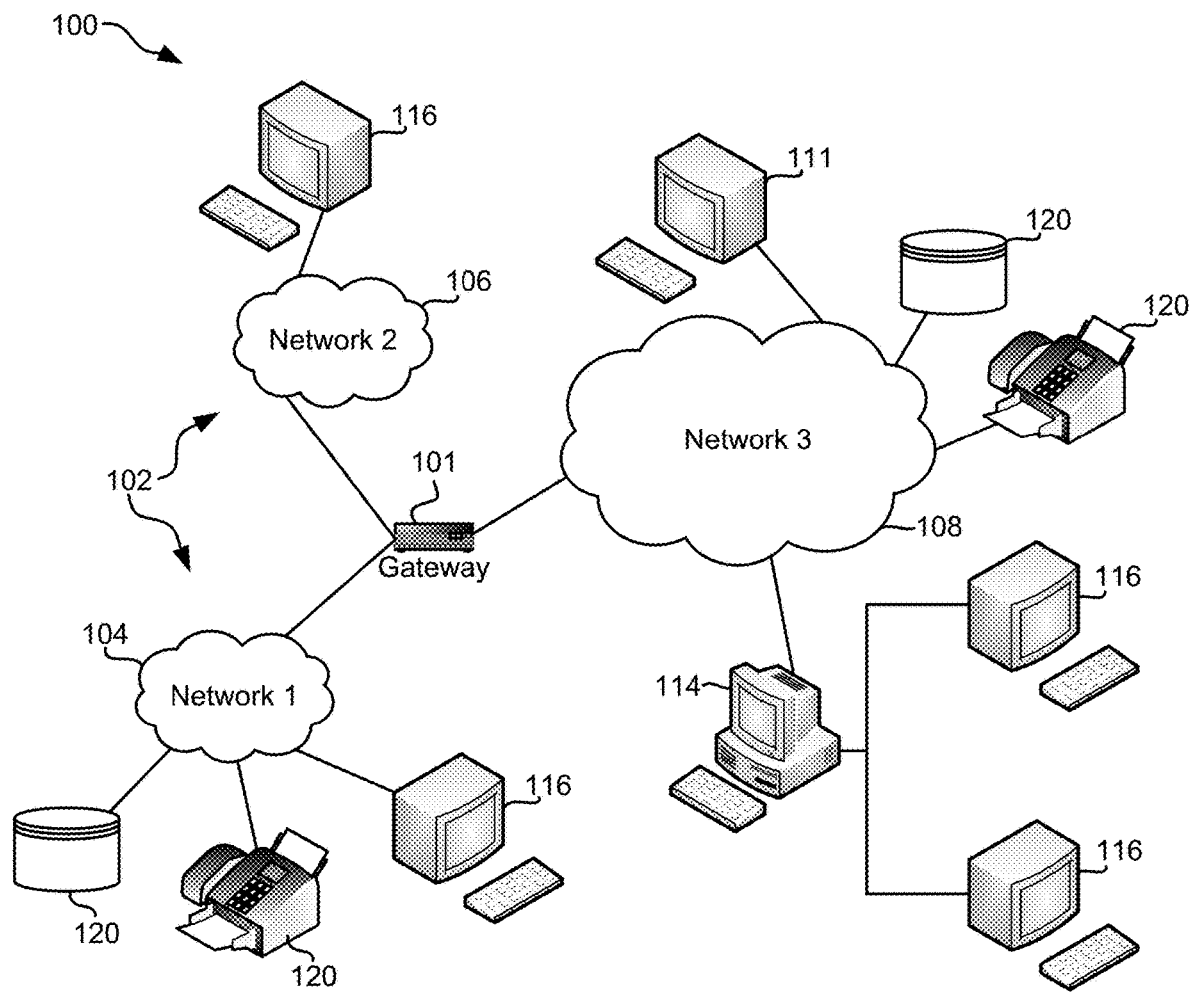
FIG. 1 illustrates a network architecture 100, in accordance with one embodiment.

The following description discloses several preferred embodiments of systems, methods and computer program products for adjusting aspects of a moving platform. Various embodiments provide a method to provide personalized health care to patients based on demographics, historical health care information for a given patient, patient population, and/or family history, relevant medical literature, and practical considerations such as financial and technological resource constraints.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified. It will be further understood that the terms "includes" and/or "comprising," when used in this specification, specify the presence of stated features, integers, steps, operations, elements, and/or components, but do not preclude the presence or addition of one or more other features, integers, steps, operations, elements, components, and/or groups thereof.

The term "independently" as recited herein and applied to members of a group, e.g. one or more labels each independently corresponding to a known cause of a particular health condition, is to be understood as meaning each member of the group individually satisfies the stated condition. In the context of the foregoing example, each label corresponds to a known cause of a particular health condition, but different labels may correspond to different health conditions, or the same health condition, in any possible combination or permutation that would be appreciated by a person having ordinary skill in the art upon reading the present disclosures.

The term "structured," and particularly "structured data" refers to information having a fixed form or constrained set of possible values. Structured information is organized, e.g. in a particular data structure such as a database, form, or the like. Structured information may include data having associated therewith descriptive metadata, e.g. metadata describing the type or source of the information represented in the value, such as identifying a value as a heart rate for a particular patient observed at a particular time and/or location. Exemplary forms of structured data may include, according to various embodiments, data structures, electronic documents (including but not limited to web pages, XML documents, word processing documents, spreadsheets, etc. having an underlying structure defined therein), curated/annotated images (e.g. images of forms annotated with metadata fields describing each field and/or defining suitable values/format/etc.), certain electronic health care records (e.g. records in a database having a predefined structure), etc. as would be appreciated by a skilled artisan upon reading the instant descriptions.

The term "unstructured," and especially "unstructured data" refers to information that lacks any of the constraints, organization, and/or associated metadata characteristic of structured data. Put another way, "unstructured" information is "free-form" information. Unstructured data may, for example, take the form of as-is digital images, e.g. scanned or otherwise digitized images of health care records, medical publications, or other documents, X-ray scans or other medical images, videos (e.g. MRIs, CT scans, sonograms, etc.), handwritten notes, certain electronic health care records (e.g. records lacking any structure or associated metadata), audio data such as a physician's dictation, patient interview or statement, and transcriptions thereof, etc. as would be appreciated by a person having ordinary skill in the art upon reading the present descriptions.

As discussed herein, the terms "wearable," "device" and "sensor" are to be understood as synonymous, and refer generally to smart devices that are optionally but preferably integrated with various accessories such as garments, wrist bands, eyeglasses, etc. and/or integrated with other devices such as wristwatches, headphones and smartphones. Wearables are used for monitoring one or more health conditions of a particular individual from a distance, saving time, improving care, and reducing overall cost of medical needs. Wearable devices may include any combination of chemical sensors, mechanical sensors, electrical sensors, optical sensors, pressure sensors, etc. as would be appreciated by a skilled artisan after reading the instant disclosure. Exemplary wearables may include various Internet of Things (IoT) devices, such as wirelessly connected glucometers, scales, heart rate monitors, blood pressure monitors, potentiometers, thermometers or other temperature-sensing devices, gyroscopes, accelerometers, cameras, microphones, etc. as would be understood by a person having ordinary skill in the art upon reading the present descriptions. Wearables may also include any suitable devices configured for and/or utilized in monitoring real time medical procedures, such as may be used in an intensive care unit (ICU) procedure.

The term "metric" as utilized herein shall be understood as referring to any characteristic relating to the health of a patient, preferably measurable characteristics. Exemplary metrics may include weight, heart rate, blood pressure, presence/concentration of one or more markers or chemicals of interest, such as gene expression levels, cholesterol levels, etc., disease diagnosis and/or progression, posture, gait, respiration rate, or any other indicator of a patient's medical status, as would be understood by a person having ordinary skill in the art upon reading the instant descriptions.

The term "value", particularly when referring to a metric, indicates a particular state or measurement of the corresponding metric at a given time. For example, suitable values of the metric "weight" may be any numerical value indicating the patient's weight, such as 150 pounds, 100 kilograms, 20 stone, etc. in various embodiments. The metric "heart rate" may be represented by values expressed in beats per minute (bpm), e.g. 42 bpm, 70 bpm, etc. Values need not necessarily be numerical. For example, disease diagnosis values may be expressed in textual and/or numerical terms, such as "adult onset diabetes positive" or a stage number to indicate progression of an oncological condition. Those having ordinary skill in the art will appreciate that values may include any form of expressing the various possible states/conditions of a given metric in accordance with various embodiments and without departing from the scope of the inventive concepts presented herein.

Figure 3:
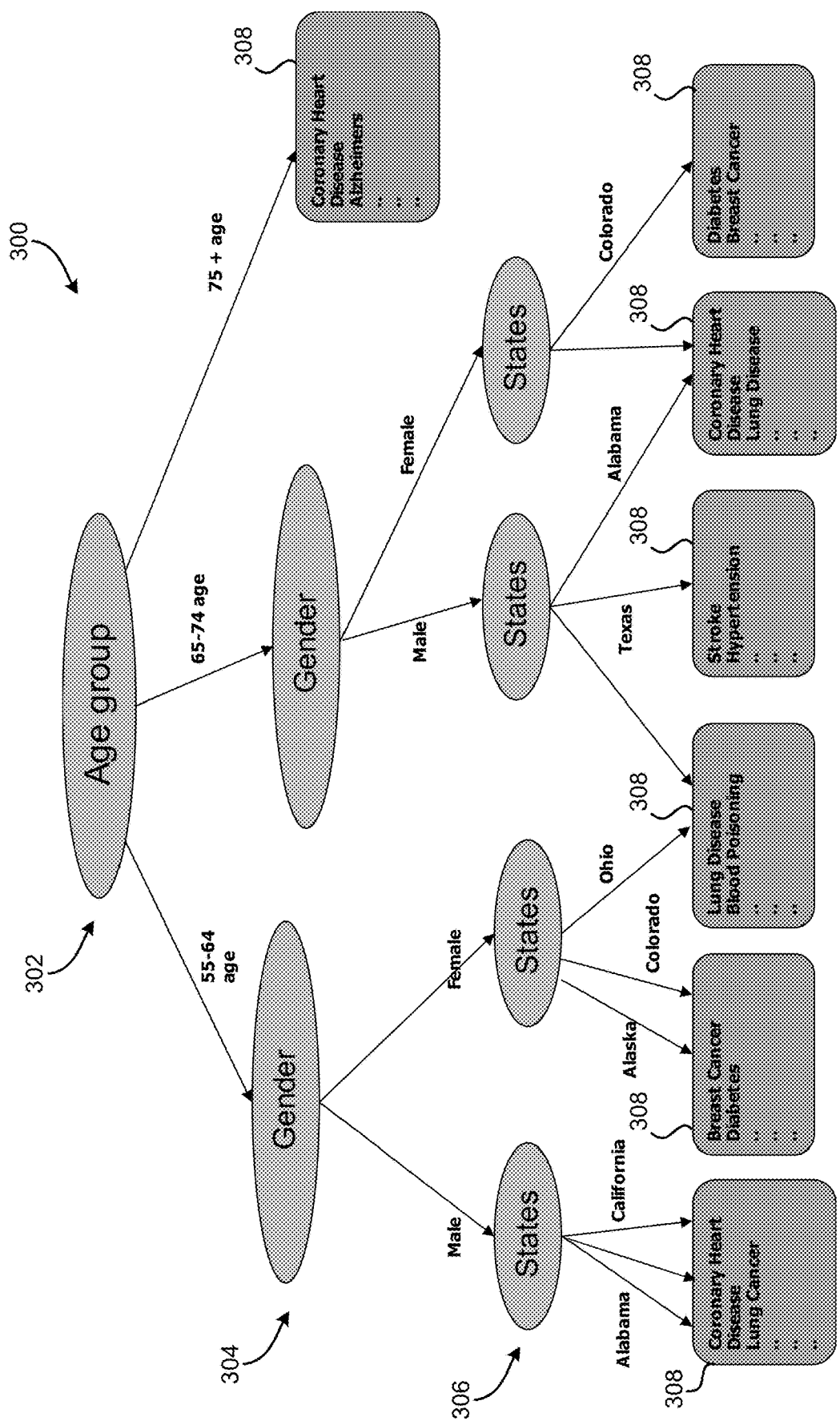
FIG. 3 illustrates a decision tree 300 for modeling and predicting relevant health conditions based at least in part on demographics, in accordance with one embodiment.

The term "demographic" and "demographics" refers to any characteristic that may be utilized to divide a population into subpopulations. Demographics may be mutable or immutable, and may include medical and/or (apparently) non-medical information. Exemplary demographics in accordance with preferred embodiments of the inventive concepts described herein include age, gender, geographic location, diseases status and/or family history, race/ethnicity, occupation, etc. as would be understood by a person having ordinary skill in the art upon reading the present descriptions. Demographics are structured information, in that each category is represented by only a finite number of possible states or values. For example, the demographic "gender" may be a binary category having values "male" and "female." The demographic "geographic location" may have one of a set number, e.g. fifty, possible values, each corresponding to a particular geographic area such as a state, province, town, elevation level, climate type, etc. as would be understood by a person having ordinary skill in the art upon reading the present descriptions. Exemplary demographics are shown in FIG. 3 in accordance with one particular implementation of the inventive concepts presented herein.

The following description discloses several preferred embodiments of systems, methods and computer program products for providing personalized health care to patients based on demographics, historical health care information for a given patient, patient population, and/or family history, relevant medical literature, and/or practical considerations such as financial and technological resource constraints. More particularly, techniques for predicting likely health conditions for a patient based on the foregoing inputs, as well as recommending suitable wearable technology to observe occurrence and/or progression of or toward particular health conditions while remaining within the practical constraints are proposed.

In providing personalized health care to a particular patient population, it is advantageous to predict the major causes of health issues associated with particular patients based on a large dataset including any combination of demographic information, personal health history, health history of relevant patient populations (e.g. family history, history of individuals with similar genetic profile, etc.), results of a particular case study or set of case studies, etc. as would be appreciated by a person having ordinary skill in the art upon reading the present descriptions. Given the historical data about demography and personal health, the presently disclosed inventive concepts involve identifying relationships between different demographic attributes and personal health history; predicting the major causes of health issues (e.g. risk factors) associated with health conditions likely to be experienced by the particular patient based on their demographics, genetics, health history, etc.; and recommend personalized health care accordingly. The personalized health care may include treatment, preventative medicine, and/or observation of biological characteristics (e.g. pulse, blood pressure, cholesterol levels, breathing rate and/or volume, concentration of particular compounds in particular locations or media within the body such as specific oxygen in blood, gene expression levels in particular cell types or organs, etc. as would be understood by a person having ordinary skill in the art of diagnostic and/or predictive medicine, according to various embodiments) using suitable wearable technology.

Accordingly, the presently disclosed inventive concepts represent a technological improvement to the field of diagnostic and/or preventative medicine, in that likely health conditions that a particular patient may exhibit can be predicted with confidence based on demographics of the patient and a large volume of health data, both structured and unstructured, and optionally organized according to demographics or other delimiting features to determine various populations or subpopulations according to the value of the delimiting feature. For instance, features taken into consideration to identify/predict likely health care conditions and/or delimit different populations/subpopulations may include ethnic group of the patient, health history, illness history, genetic information, DNA structure, place of birth, gender, age, location, etc. as described herein, and equivalents thereof that would be appreciated by a person having ordinary skill in the art upon reading the present disclosure.

Moreover, as understood herein the various features may be employed in any combination or permutation without departing from the scope of the inventive concepts presented herein. These features may serve as the basis for forming decision trees that separate categories of individuals based on factors other than demographics, in alternative embodiments of decision tree 300 as shown in FIG. 3 and described in greater detail below.

Furthermore, upon identifying likely health conditions for a particular patient, associated potential causes, risk factors, etc. corresponding to the likely health conditions may be determined, e.g. based on textual analysis of a vast volume of medical and/or academic publications and/or medical data, and appropriate monitoring, treatment, etc. may be recommended in a personalized manner to provide the best quality of care to the patient.

Notably, conventional diagnostic and preventative medicine techniques are incapable of providing the level of confidence in predicting likely health conditions and recommending appropriate monitoring or treatment, because it is practically impossible for health practitioners to parse the vast amount of data represented in the publications and/or medical data. Accordingly, physicians, nurses, and other health care professionals are not capable of reviewing all the pertinent information for each possible combination of factors, e.g. family medical history, personal medical history, demographics, etc. that may provide a useful prediction as to likely health conditions and appropriate monitoring for the patient. As a result, health care professionals typically limit diagnoses, prognoses, etc. based on the health care records for the individual patient, coupled with the professional's personal knowledge and experience. The presently disclosed inventive concepts represent an improvement over this conventional paradigm by expanding the data considered in predicting health conditions beyond a patient's individual records and a professional's personal knowledge and experience to include data corresponding to a large number of patients sharing the same set of demographics, health histories, genetics, etc. as the patient for which the health condition is to be predicted.

Moreover, with particular respect to monitoring, medical and academic literature relating to particular health conditions may not include information regarding appropriate wearable technology that may be utilized to monitor progression or occurrence of a likely health condition. As such, health care professionals, even if capable of reviewing the vast body of literature and data to determine appropriate likely health conditions based on demographics, historical health information, relevant medical literature, etc., may not be privy to corresponding information regarding wearable technology. Thus, providing a robust system and techniques for integrating information regarding wearable technology with medical information such as present in publications and medical databases represents a further technological improvement to the field of preventative and diagnostic medicine.

Health care services is a vitally important industry, and only becomes more so in light of the baby-boomer generation approaching the age range associated with many common diseases such as coronary heart disease, cancer, and various degenerative diseases. The drastic increase in the patient population associated with this transition will put great stress on the already-struggling industry. Health care professionals will need to improve the efficiency with which they can provide quality care to their growing body of patients, lest quality of care suffer due to the added strain. The presently disclosed inventive concepts facilitate improving quality of care by enabling health care professionals to leverage vast quantities of historical medical and demographic information in conjunction with information about wearable technology in order to predict likely health conditions based on patient demographics, historical health care information for the patient and/or a given patient population, relevant medical literature, etc., as well as integrate these predictions with appropriate monitoring via wearable technology that complies with any applicable financial and/or technological constraints of the patient and/or operating environment.

Thus, in various embodiments of the presently disclosed inventive concepts, the prediction of likely health conditions for a particular patient are based at least in part on relationships identified between different demographics attributes and associated health conditions, e.g. from a historical dataset; and the patient's personal health history.

In one general embodiment, a computer program product for providing personalized recommendations of devices for monitoring and/or managing a health condition includes a computer readable storage medium having program instructions embodied therewith, where the computer readable storage medium is not a transitory signal per se. The program instructions are executable by a processor to cause the processor to perform a method including: receiving, at the processor, first structured information regarding a patient and a first set of one or more patient populations; receiving, at the processor, unstructured information regarding at least the patient and a second set of one or more patient populations; analyzing, by the processor, the unstructured information to derive second structured information; determining, by the processor one or more health metrics to be monitored for the patient based on analyzing the first structured information and the second structured information using a classification model; and determining, by the processor, an optimum set of devices to be used for monitoring the one or more health metrics.

In accordance with another general embodiment, a computer-implemented method for providing personalized recommendations of devices for monitoring and/or managing a health condition includes: receiving first structured information regarding a patient and a first set of one or more patient populations; receiving unstructured information regarding at least the patient and a second set of one or more patient populations; analyzing the unstructured information to derive second structured information; determining one or more health metrics to be monitored for the patient based on analyzing the first structured information and the second structured information using a classification model; and determining an optimum set of devices to be used for monitoring the one or more health metrics.

In yet another general embodiment, a system for providing personalized recommendations of devices for monitoring and/or managing a health condition includes a processor and logic in and/or executable by the processor to cause the processor to: receive first structured information regarding a patient and a first set of one or more patient populations; receive unstructured information regarding at least the patient and a second set of one or more patient populations; analyzing the unstructured information to derive second structured information; determine one or more health metrics to be monitored for the patient based on analyzing the first structured information and the second structured information using a classification model; and determine an optimum set of devices to be used for monitoring the one or more health metrics.

General Computing/Networking Concepts

FIG. 1 illustrates an architecture 100, in accordance with one embodiment. As shown in FIG. 1, a plurality of remote networks 102 are provided including a first remote network 104 and a second remote network 106. A gateway 101 may be coupled between the remote networks 102 and a proximate network 108. In the context of the present architecture 100, the networks 104, 106 may each take any form including, but not limited to a LAN, a WAN such as the Internet, public switched telephone network (PSTN), internal telephone network, etc.

In use, the gateway 101 serves as an entrance point from the remote networks 102 to the proximate network 108. As such, the gateway 101 may function as a router, which is capable of directing a given packet of data that arrives at the gateway 101, and a switch, which furnishes the actual path in and out of the gateway 101 for a given packet.

Further included is at least one data server 114 coupled to the proximate network 108, and which is accessible from the remote networks 102 via the gateway 101. It should be noted that the data server(s) 114 may include any type of computing device/groupware. Coupled to each data server 114 is a plurality of user devices 116. User devices 116 may also be connected directly through one of the networks 104, 106, 108. Such user devices 116 may include a desktop computer, lap-top computer, hand-held computer, printer or any other type of logic. It should be noted that a user device 111 may also be directly coupled to any of the networks, in one embodiment.

A peripheral 120 or series of peripherals 120, e.g., facsimile machines, printers, networked and/or local storage units or systems, etc., may be coupled to one or more of the networks 104, 106, 108. It should be noted that databases and/or additional components may be utilized with, or integrated into, any type of network element coupled to the networks 104, 106, 108. In the context of the present description, a network element may refer to any component of a network.

According to some approaches, methods and systems described herein may be implemented with and/or on virtual systems and/or systems which emulate one or more other systems, such as a UNIX system which emulates an IBM z/OS environment, a UNIX system which virtually hosts a MICROSOFT WINDOWS environment, a MICROSOFT WINDOWS system which emulates an IBM z/OS environment, etc. This virtualization and/or emulation may be enhanced through the use of VMWARE software, in some embodiments.

In more approaches, one or more networks 104, 106, 108, may represent a cluster of systems commonly referred to as a "cloud." In cloud computing, shared resources, such as processing power, peripherals, software, data, servers, etc., are provided to any system in the cloud in an on-demand relationship, thereby allowing access and distribution of services across many computing systems. Cloud computing typically involves an Internet connection between the systems operating in the cloud, but other techniques of connecting the systems may also be used.

Figure 2:
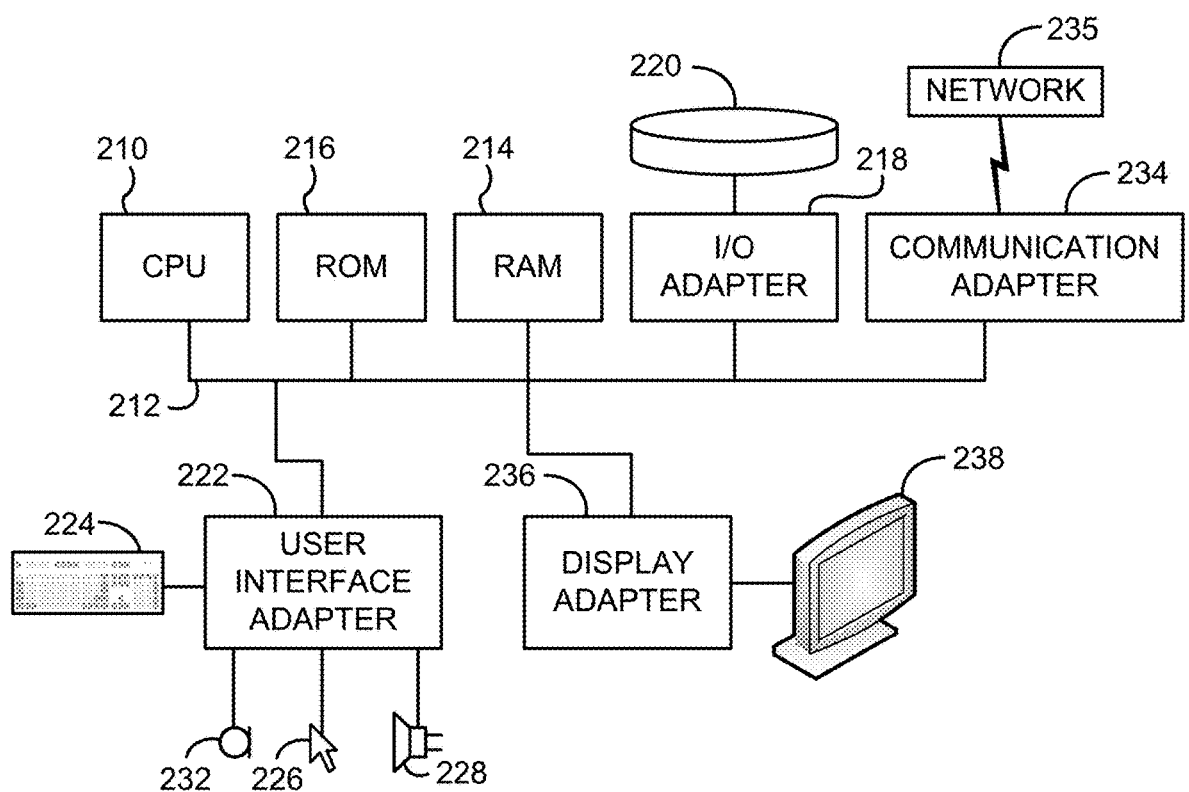
FIG. 2 shows a representative hardware environment 200 that may be associated with the servers and/or clients of FIG. 1, in accordance with one embodiment.

FIG. 2 shows a representative hardware environment associated with a user device 116 and/or server 114 of FIG. 1, in accordance with one embodiment. Such figure illustrates a typical hardware configuration of a workstation having a central processing unit 210, such as a microprocessor, and a number of other units interconnected via a system bus 212.

The workstation shown in FIG. 2 includes a Random Access Memory (RAM) 214, Read Only Memory (ROM) 216, an I/O adapter 218 for connecting peripheral devices such as disk storage units 220 to the bus 212, a user interface adapter 222 for connecting a keyboard 224, a mouse 226, a speaker 228, a microphone 232, and/or other user interface devices such as a touch screen and a digital camera (not shown) to the bus 212, communication adapter 234 for connecting the workstation to a communication network 235 (e.g., a data processing network) and a display adapter 236 for connecting the bus 212 to a display device 238.

The workstation may have resident thereon an operating system such as the Microsoft Windows® Operating System (OS), a MAC OS, a UNIX OS, etc. It will be appreciated that a preferred embodiment may also be implemented on platforms and operating systems other than those mentioned. A preferred embodiment may be written using XML, C, and/or C++ language, or other programming languages, along with an object oriented programming methodology. Object oriented programming (OOP), which has become increasingly used to develop complex applications, may be used.

As discussed herein, logic may be implemented as a method on any device and/or system or as a computer program product, according to various embodiments.

In various embodiments, the present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which includes one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Moreover, a system according to various embodiments may include a processor and logic integrated with and/or executable by the processor, the logic being configured to perform one or more of the process steps recited herein. By integrated with, what is meant is that the processor has logic embedded therewith as hardware logic, such as an application specific integrated circuit (ASIC), a FPGA, etc. By executable by the processor, what is meant is that the logic is hardware logic; software logic such as firmware, part of an operating system, part of an application program; etc., or some combination of hardware and software logic that is accessible by the processor and configured to cause the processor to perform some functionality upon execution by the processor. Software logic may be stored on local and/or remote memory of any memory type, as known in the art. Any processor known in the art may be used, such as a software processor module and/or a hardware processor such as an ASIC, a FPGA, a central processing unit (CPU), an integrated circuit (IC), a graphics processing unit (GPU), etc.

It will be clear that the various features of the foregoing systems and/or methodologies may be combined in any way, creating a plurality of combinations from the descriptions presented above.

It will be further appreciated that embodiments of the present invention may be provided in the form of a service deployed on behalf of a customer to offer service on demand.

As noted briefly above, and as will be described in further detail below with reference to FIGS. 3-5, the presently disclosed inventive concepts generally entail collecting structured and unstructured information about a particular patient and/or suitable patient populations (e.g. populations representing different demographic segments, different personal and/or family medical histories, different genotypes/phenotypes, etc. for one or more portions of an overall patient populace, etc. as described herein). This information is analyzed using a classification model trained by machine learning techniques to identify suitable metrics to monitor so as to track and predict the health status of a given patient.

The metrics are preferably considered according to an optimization model to evaluate an optimum device or set of devices that are configured to monitor the metrics while operating within particular practical constraints such as available computational and/or networking resources and financial limitations. This optimization enables identification of the most appropriate set of devices to employ for health monitoring with respect to a particular patient given the available medical information and practical limitations, and allows consideration of a vast array of potential device/metric combinations so as to improve health care monitoring and disease prevention.

Moreover, in order to adapt to ongoing changes in a patient's health over time, event triggers may be set and updated recommendations generated in response to detecting an event trigger. The updated recommendations may take into account new/additional patient medical information, e.g. metric values monitored since a previous recommendation was issued, to give the most relevant set of devices to use for future monitoring. For example, if a patient at risk of coronary heart disease exhibits a blood pressure, cholesterol level, heart rate, or any combination thereof in excess of a predetermined threshold value (e.g. a value indicative of disease status or progression, such as may be defined in medical literature), this may trigger an update wherein information gathered in the period leading up to the trigger event (e.g. days, weeks, months, years, depending on the nature of the condition and availability of data) is fed into the classification model to identify new metrics and/or reinforce importance of existing metrics to be monitored going forward.

Accordingly, the inventive concepts presented herein include the use of structured and unstructured information to generate a set of health care metrics to be monitored for a particular patient; determining an optimal device or set of devices configured to monitor the metrics while complying with practical constraints such as available resources (financial and/or technological); and detecting the occurrence of trigger events that may indicate a change in health status; and generating new recommendations based on additional information upon detecting a trigger event, e.g. generating a new recommendation taking into account the metrics monitored for the patient in a period leading up to the trigger event.

Processing Structured Data

In preferred embodiments, the presently described inventive concepts include processing structured data relating to a patient's health so as to build a suitable knowledge base from which to identify suitable metrics for monitoring health condition(s) of the patient. Exemplary structured information may include medical and/or non-medical information, and preferably includes at least demographics for the patient and an appropriate patient population. Demographics may be obtained from public sources of any type that would be appreciated as suitable by a skilled artisan upon reading the present disclosures. Other structured information such as patient/family medical history, medical information associated with a particular population or subpopulation, etc. may be obtained from medical literature, scientific literature, technical reports, and any other equivalent or suitable source of structured information regarding health, as would be appreciated by those having ordinary skill in the art upon reading the present descriptions.

Processing structured information generally involves parsing the various inputs and organizing the data points into various categories represented by the population. In some approaches, structured data may not need to be processed to be intelligible according to the classification model, and in such cases may be simply provided as input to a classification model for identification of metrics to be monitored.

Processing/Analyzing Unstructured Information

Unstructured information should be processed/analyzed prior to being input to the classification model, in preferred approaches. In essence, processing/analyzing unstructured information includes analyzing the various data points to determine which portions of the unstructured information are relevant to a patient's medical status, and identifying the particular value, condition, etc. for proper consideration by the classification model. For example, analyzing unstructured information may involve analyzing images and/or videos to determine if a patient exhibits a particular condition. Such image analysis may be performed using any suitable technique known in the art. In more embodiments, analyzing unstructured information may include textual analysis, e.g. of handwritten notes in a patient's chart, medical literature, etc. The textual information may be evaluated using a text mining model such as a Term Frequency-Inverse Document Frequency (tf-idf) or equivalent model. In various embodiments, analyzing unstructured information essentially includes extracting features from the data that are relevant to monitoring health status, which may be utilized to train the text mining and/or natural language processing models for subsequent classification of sample or dataset having unknown classification(s).

In preferred approaches, historical demographic and/or medical data including a plurality of attributes are analyzed. For example, historical demographic data may include any combination of demographic attributes discussed herein, and is preferably associated with causes of health conditions experienced by the individuals represented within the historical demographic data. Historical medical data may include information concerning the medical histories of one or more patient populations, medical literature, historical information concerning the patient, such as medical history, diagnosed illnesses, genetic information, etc. as described in greater detail hereinabove. In preferred embodiments, the historical demographic data may be received in the form of a text string, which may be parsed from literature, publicly available medical databases, private medical databases, health care records, or any other suitable source of historical medical and/or demographic information and optionally formatted according to a desired convention using any suitable techniques that would be appreciated by persons having ordinary skill in the art of textual information parsing and formatting upon reading the present descriptions. In one embodiment world health organization (WHO) data may be the source of the historical medical and/or demographic information.

Classification Model

Structured and unstructured data are preferably provided as input to a classification model, which is preferably a machine learning classification model that maps the health history, demographic features and the existing monitoring data from sensors and applications available for the user.

The presently disclosed inventive concepts include the use of one or more machine learning classifiers train on the features of the system, such as the structured information obtained and/or derived for the representative patient populations. The classifier model learns and identifies the right measurements that need to be monitored in the system. In one embodiment, the classifier is trained on features found to accurately predict the diseases that person is at risk for, e.g.: the current values of the measured attributes of the individual's health, the individual's demographics information such as age, gender, location of residence, ethnicity, etc. which may be in the form of structured data, as well as the person's Electronic Health Record (EHR) which determine the previous illnesses that the patient has suffered.

The EHR set of data is typically a textual un-structured format. Thus, building a text mining model using, e.g., the Term Frequency-Inverse Document Frequency (tf-idf) algorithm, allows structuring of unstructured data (or equivalently deriving structured information from unstructured data). The basic idea is that the algorithm identifies a bag of words that are most helpful in predicting the corresponding at-risk diseases. The importance of a word increases proportionally to the number of times it appears in the document but is offset by the frequency of the word in the corpus. The algorithm counts the frequency of any of these words and uses that as an additional structured feature for the classification model along with the demographics data.

Preferably, the training set provided to the classification model includes historical demographic data for the patient population(s). Furthermore, the historical demographic data may be associated with one or more labels each independently corresponding to a known cause of a particular health condition. In various approaches, each demographic value may be associated with a label, and/or combinations of demographic values may be associated with a label. Deciding the particular labels to apply to particular demographic(s) may be based in whole or in part on training a model using a decision tree algorithm $(x, Y)=(x_1, x_2, x_3, x_4, \ldots x_n, Y)$ as described herein with reference to FIG. 3.

In more embodiments, the labels may additionally or alternatively correspond, independently, to risk factors associated with particular health issues, such as environmental, behavioral, genetic, geographic, etc. risk factors including as exemplars such as consumption of particular substances (e.g. tobacco, alcohol, medications, etc.); lifestyle (e.g. active, sedentary, risk-seeking); travel history or planned travel (especially abroad); mutations or genetic expression information; etc. as would be appreciated by a person having ordinary skill in the art upon reading the instant disclosure.

Thus, the presently described inventive concepts may involve building a decision tree model based at least in part on the historical demographic data and the one or more labels associated therewith, along with any other suitable structured information and optionally associated labels. The decision tree model may be constructed top-down (i.e. root to leaf) based on a training dataset D comprising the historical medical and/or demographic information. Moreover, the entropy and/or information gain may be computed for each attribute $A_i$ used for partitioning the decision tree at a given level of the tree. As understood herein, the entropy E may be defined as $E[D]=-\Sigma P(c_j) \log_2 P(c_j)$, while the information gain G may be defined as $G(D, A_i)=E[D]-E_{Ai}[D]$, and $P(c_j)$ is the probability of an element belonging to class $c_j$ in the dataset D.

Preferably, the Attribute $A_i$ that has the maximum Information Gain G for a given tree level is used to split the current tree, while minimizing the uncertainty to partition the dataset into different classes at that level. For example, and with reference to the exemplary embodiment of FIG. 3, the Attribute Value "Coronary Heart Disease" is the major cause of health issue in patients belonging to the demographic group of individuals age 75 or older. Hence, this attribute (age) has the maximum Information Gain for the Decision Tree branch of Age-Group 75 and above, and may be employed as the demographic attribute represented by the root node of the decision tree.

Additionally, a vector $Y_k$ representing one or more most probable causes of one or more of a plurality of health conditions may be generated based at least in part on the decision tree model. The model, according to one illustrative approach, yields a vector $Y_k$ of causes of health issues or conditions $y_i$ and corresponding probabilities $p_i$, and takes the following form: Y: $(y_1: p_1, y_2: p_2, y_3: p_3, \ldots, y_n: p_n)$. This vector $Y_k$ may be sorted based on $p_i$ to compute the top-k causes of health issues or conditions. Subsequently, $Y_k$ may be provided for comparison to a second vector $Z_k$.

In various approaches, building the decision tree model; generating the vector $Y_k$; and/or maximizing the information gain G while minimizing the entropy E may be based on a clustering of demographic values and/or attributes, the clustering being generated based on the historical medical and/or demographic information represented in dataset D. The clustering may be performed using any suitable technique that would be appreciated by a person having ordinary skill in the art upon reading these descriptions, without departing from the scope of the inventive concepts presented herein.

Accordingly, one or more most likely health conditions for a patient may be estimated based on comparing the vector $Y_k$ to a second vector $Z_k$, where $Z_k$ represents one or more most probable causes of one or more of the plurality of health conditions determined based on a health care record for the patient. Similar to $Y_k$, the second vector $Z_k$ may take the following general form: $Z_k$: $(z_1: p_1, z_2: p_2, z_3: p_3, \ldots, z_k: z_k)$. Preferably, the comparison of $Y_k$ and $Z_k$ includes computing either a union, an intersection, or both, of $Y_k$ and $Z_k$. The union advantageously represents and predicts the top k health conditions that should be accounted for via appropriate treatment, monitoring, etc., while the intersection predicts a health plan with lesser coverage, but which may be more economically viable for the patient.

Now referring to FIG. 3, an exemplary classification model is provided in the form of a decision tree 300 for modeling and predicting relevant health conditions, according to one embodiment. While the tree 300 shown in FIG. 3 is demographic information, in various embodiments other types of structured information may be employed in the context of classification models consistent with the presently described inventive concepts.

With continuing reference to FIG. 3, the decision tree 300 includes three levels 302, 304, 306 each corresponding to a particular demographic attribute and a plurality of leaf nodes 308 each corresponding to one or more health conditions historically associated with patients satisfying a particular combination of demographic attributes. The internal nodes of the decision tree 300 each represent a division among possible values for a particular demographic attribute corresponding to the respective layer 302, 304, or 306 of the decision tree 300. In more embodiments, classification models such as decision tree 300 may take into account additional structured information such as may be derived from electronic health care records to determine associations between particular metrics and corresponding health status.

For example, in accordance with the embodiment shown in FIG. 3, layer 302 comprises a root node corresponding to the demographic attribute of "age" and represents a division according to one or more predetermined age groups that may be used to identify or eliminate relevant health conditions corresponding to each age group.

Layer 304, meanwhile, comprises two internal nodes and a leaf node 308 each corresponding to one of the age groups defined by the root node in layer 302. Those having ordinary skill in the art will appreciate that the decision tree 300 therefore need not be symmetric, and leaf nodes 308 may be present at various levels of a decision tree according to various embodiments of the presently disclosed inventive concepts.

According to the embodiment of FIG. 3, the internal nodes for layer 304 each correspond to the demographic attribute of "gender" (which, in the context of the present disclosures, may refer to biological characteristics, e.g. in the case of physical health conditions such as cancer, cardiovascular health conditions, reproductive health conditions, etc.; or identity characteristics, e.g. in the case of mental health conditions such as post-traumatic stress disorder, depression, etc.) and represent a division between the age groups reflected in layer 302 according to gender.

Meanwhile, the leaf node 308 of layer 304 corresponds to known, likely health conditions (Preferably, the known health conditions in the leaf nodes are the most likely K health conditions for a particular demographic or combination of demographics, where K is a predetermined number of health conditions determined relevant to report, e.g. based on the K health conditions corresponding to a predetermined threshold frequency, percentage, etc. of occurrence within the associated demographic, and/or based on a severity of the health condition(s)) to be experienced by members of the corresponding demographic. In one embodiment, K=5.

For instance, in the embodiment represented by FIG. 3, persons of a predetermined age or older (e.g. 75 years of age or more) may have a certain, high likelihood of experiencing one or more health conditions such as coronary heart disease, Alzheimer's disease, Parkinson's disease, etc. regardless of the person's gender, or place of residence. Accordingly, to maximize computational efficiency of providing relevant recommendations for personalized health care, the decision tree 300 may be built so as to predict the corresponding health conditions based on age alone. Of course, other dispositive demographics or demographic attributes may be employed with respect to different health conditions without departing from the scope of the presently disclosed inventive concepts. As referenced herein, demographic attributes should be understood to encompass a broad category within which various demographic groups may be defined, and demographics refer to the actual demographic group(s) to which various individuals may belong within a particular demographic attribute. For example, a demographic attribute of "age" may include demographics of 0-18, 19-29, 30-39, 40-54, 55-64, 65-74, and 75+.

For other health conditions which may be predicted with greater accuracy or certainty based on additional demographic information, the leaf nodes 308 may reside further down the tree. Accordingly, and with respect to the embodiment of FIG. 3, level 306 includes a plurality of internal nodes each corresponding to a demographic attribute of "current location of residence," and represent a plurality of different possible places where individuals may reside.

The possible places may be defined with any appropriate granularity that would be appreciated by persons having ordinary skill in the art of diagnostic and/or predictive medicine, and preferably are defined with a granularity that provides the greatest medical relevance to predicting health conditions for a particular patient population. For example, for an international patient population the particular places may include different countries, continents, regions (e.g. tropical, temperate, desert, mountain, jungle, island, etc.), while within a particular country the possible places may include different states, provinces, territories, etc., and while for a particular state the possible places may include different cities, municipalities, etc. As shown in FIG. 3, the internal nodes of level 306 reflect different states where an individual may reside within the United States of America.

With continuing reference to decision tree 300 as represented in FIG. 3, the leaf nodes 308 following level 306 represent the K most likely health conditions for patients satisfying the particular combination of age group, gender, and place of residence reflected by the progression from the root node in level 302 to the respective leaf node 308. For instance, according to leaf node 308 male patients aged 55-64 and living in Alabama, California, or Texas may be most likely to experience coronary heart disease and/or lung cancer, and these conditions may be predicted for patients within this demographic. As will be discussed in further detail below regarding method 500, a particularly advantageous aspect of the presently disclosed inventive concepts is to recommend personalized monitoring using appropriate wearable technology to monitor the progression or occurrence of the likely health conditions for the particular patient. This in turn allows earlier detection and treatment of such conditions, improving the duration and quality of life for the patient.

Preferably, the decision tree 300 is built so as to provide the best possible separation of possible health conditions as high in the tree (i.e. as close to the root node) as possible. As such, the root node preferably represents the demographic attribute that is most dispositive with respect to identifying a particular health condition. For example, different decision trees may be employed to determine most likely health conditions associated with different classes of diagnoses.

In one embodiment, a decision tree configured to determine likely health conditions associated with a particular type of disease known to only affect members of a particular demographic may employ as the root node the corresponding demographic attribute, thereby rapidly eliminating the possibility of patients not belonging to the particular demographic being predicted to experience the health condition(s) associated with the disease that only affects members of the particular demographic. In this manner, unnecessary treatments and/or medical procedures may be avoided, saving cost to the medical industry and the patient, as well as avoiding potential risks associated with such treatments and/or procedures.

In more embodiments, the decision tree 300 may include more or less levels, e.g. based on the number of demographic attributes relevant to predicting and modeling various health conditions, such as age bracket, gender, place of current residence, income level, place of birth, type of employment, lifestyle and/or environmental risk factors, ethnicity, etc. as would be understood by a person having ordinary skill in the art of diagnostic and/or predictive medicine.

Generally speaking, invoking the decision tree 300 as an algorithm may be represented according to the expression $(x, Y)=(x_1, x_2, x_3, x_4, \ldots x_n, Y)$, where $x_1$ to $x_n$ represent demographic values for n demographic attributes, and Y is a health condition associated with the particular combination of demographics represented by $x_1$ to $x_n$. Details of the algorithm will be discussed in further detail below regarding FIG. 5, according to one exemplary embodiment.

While the decision tree 300 has been described primarily with reference to structured information such as demographic information, it should be understood that various embodiments of the presently disclosed inventive concepts may build or utilize decision trees taking into account any other suitable form of structured information as defined herein without departing from the scope of those same inventive concepts.

With reference again to classification models in general, in various embodiments the classifier may be used to predict the at-risk diseases for any given person and suggest measurements that need to be taken routinely. For example, one may use a classifier algorithm to divide an input dataset into different categories of demographics based on the age-group, gender, prior health records, ethnicity, demographic state and city, occupation, and marital status. The order of demographic attributes $A_i$ is preferably selected dynamically by the algorithm to maximize the information gain G which is computed as described above.

The value of E[D] provides a way to estimate the health risk of a disease based on the frequency of the diseases using the demographic attributes $A_i$. $G(D, A_i)$ gives the information gain based on the decrease in entropy E[D] after dataset D is split on an attribute. Here, the measure of purity is called the information. It represents the expected amount of information that would be needed to specify whether a new instance should be classified for a disease or not. Entropy E[D] is a measure of impurity in information and hence works the opposite of Information Gain. Through constructing a decision tree, we find the attributes $A_i$ that return the highest information gain G. Attribute $A_i$ that has the maximum information gain G for a given tree level is used to split the current tree and minimizes the uncertainty to partition the dataset into different classes at that level. For example, attribute value "Coronary Heart Disease" is the major cause of health issue in people with age >75. Hence, it has the maximum information gain for the decision tree branch of age-group 75 and above.

It is additionaly advangateous to use the demographic attributes of the person and build the classifier model to evaluate the major health risks he can face. We form a list of measurements that can help him evaluate these risks and monitor it. The model yields the following vector of measurements that need to be monitored $y_1$ and corresponding probabilities $p_i$: Y: $(y_1: p_1, y_2: p_2, y_3: p_3, \ldots, y_n: p_n)$. We infer the personalized health track of the person that predicts the top health conditions given by Y.

In particularly advantageous embodiments, the presently disclosed inventive techniques for identifying likely health conditions based on patient demographics may be coupled with techniques for identifying appropriate devices in order to facilitate monitoring of a patient for occurrence of and/or progression toward the likely health conditions. This facilitates early detection and preventative action, by the health care professional and/or by the patient themselves, and therefore provides an improvement to the quality of care and quality of life experienced by the patient.

In one approach, a suitable method for identifying appropriate wearable technology to monitor a patient for a likely health condition is included with the classification model 404b. In accordance with identifying appropriate devices to monitor given health metrics, structured information derived from textual data, image data, and/or video data are received, the structured data being derived from one or more medical journals, publications, databases, etc. and one or more patient health care records. The information may be received in any suitable form.

Textual analytics may be applied to the received textual data, e.g. text analytics for identifying measurements (e.g. of bio-markers, vital statistics, etc.), to extract concepts from the textual data and identify relationships therebetween. For instance, in one embodiment, one or more concepts may be identified by applying one or more query rules to the textual data.

The query rules may identify keywords that establish a causal relationship between different concepts, where the concepts each independently correspond to one or more topics selected from causes, health conditions, symptoms, measurements, and wearable technologies. Thus, in a preferred embodiment, the one or more query rules each independently represent a relationship selected from: a particular cause that corresponds to a particular disease or health condition, a particular symptom that corresponds to the particular disease or health condition, a particular measurement that corresponds to the particular symptom, and a particular wearable technology that corresponds to the particular measurement, e.g. a wearable technology configured to perform the particular measurement such as pulse rate, blood sugar or insulin level, breathing rate and/or volume, neurological activity, etc. as described herein and as would be understood by a person having ordinary skill in the art upon reading the present disclosure.

For example, in one embodiment textual data may indicate: (1) lung diseases are typically caused by smoking (linking a health condition to a cause); and (2) lung disease is exemplified by symptoms including prolonged cough, expectation of sputum, blood in sputum, fatigue, weakness, shortness of breath, and/or chest pain. Textual data may also indicate (3) that a normal respiration rate is in a range from approximately 12-20 breaths per minute, and (4) an existing wearable technology is available and is configured to track a user's physical activity, breathing rate, and state of mind. From this textual data, query rules may be developed establishing relationships between the cause and the health condition (per item 1); the symptoms associated with the health condition (per item 2); the appropriate measurements to monitor the patient for occurrence and/or progression of such symptoms (per item 3); and a suitable wearable device to recommend the patient use for monitoring purposes (per item 4).

Accordingly, the presently disclosed inventive concepts may involve generating an entity relationship graph based on the concepts extracted from the unstructured information. The entity graph may take any suitable form, and preferably includes an aggregation of relationships determined by extracting the concepts from the textual data. For instance, in one embodiment the relationships may be the edges of the graph, while extracted concepts are nodes of the graph.

In one embodiment, the entity relationship graph may be searched to determine one or more measurements associated with one or more one or more most probable health conditions for the patient, e.g. based on identifying relationships between measurements and wearable technologies corresponding to the one or more most probable health conditions for the patient. The search may be performed using any suitable technique that would be appreciated by a person having ordinary skill in the art upon reading the present disclosures without departing from the scope of the inventive concepts presented herein.

Upon determining the measurements, one or more wearable technologies associated with the one or more measurements are determined, according to preferred embodiments.

The determination of wearable technology may include first determining whether any suitable wearable technology exists and is appropriate for the patient's use in monitoring their health status, and if so determining a most appropriate wearable (e.g. a wearable technology which is configured to measure the greatest number of measurements the patient should monitor) to recommend for the patient's use. A recommendation as to the patient's use of the appropriate wearable, and any appropriate services associated therewith (e.g. automated recording and reporting of data, alerts to the patient, etc.) may be rendered to the patient and/or health care professional, in some approaches.

If no appropriate wearable technology is available, the presently disclosed inventive concepts preferably include outputting an indication of such, and recommending the lack of such technology be reported, e.g. to an application or device developer who may then pursue a wearable technology to be implemented in the future and assist patients in monitoring their health status.

Optimization Model

Figure 4:
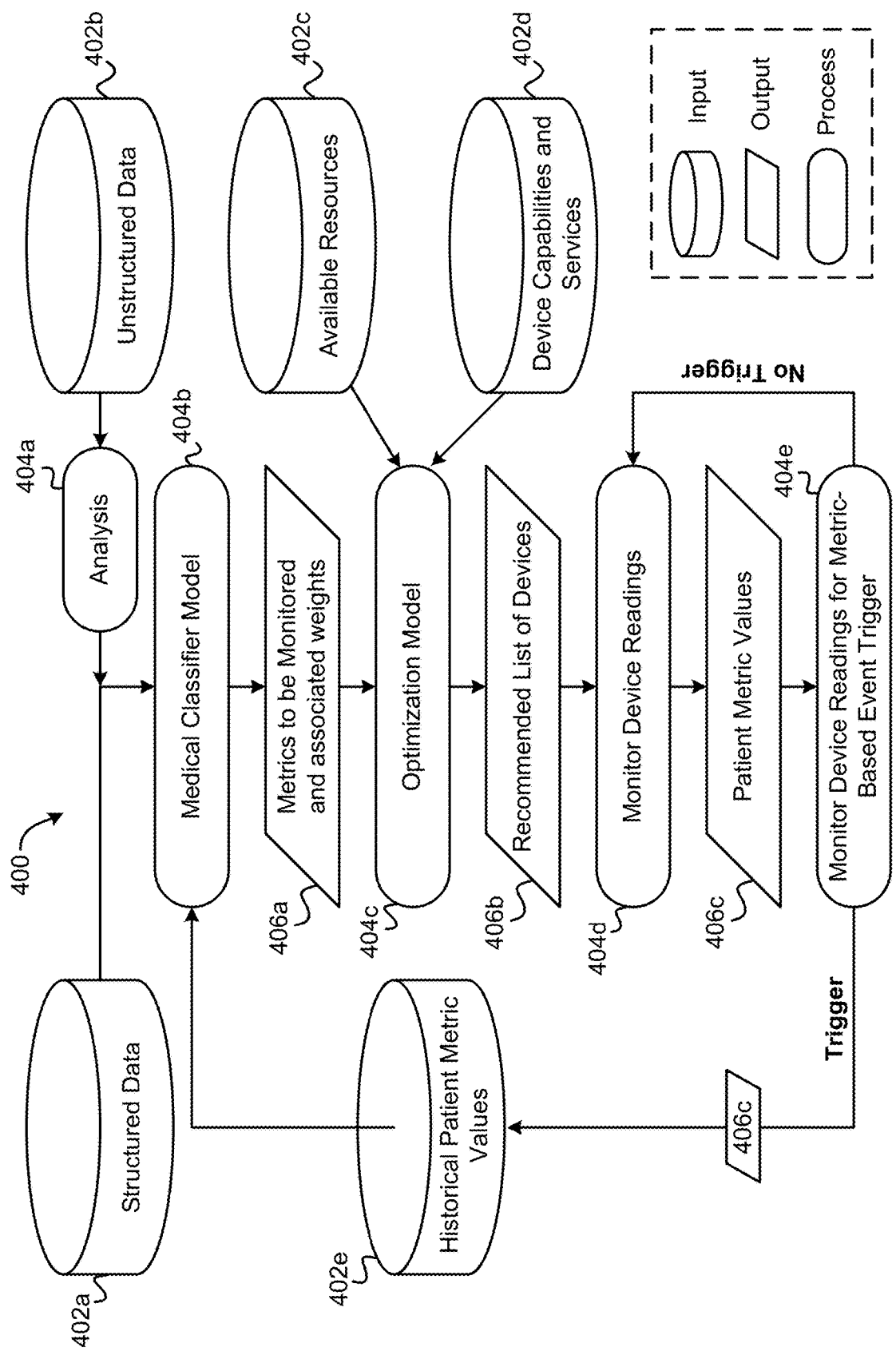
FIG. 4 is a simplified schematic of a process flow 400, corresponding inputs and outputs, and constituent processes for providing personalized recommendations for monitoring and/or managing a health condition using one or more devices, in accordance with one embodiment.

To facilitate recommendations that match a given patient's health care needs with associated practical constraints such as budgetary concerns and technological limits (e.g. network bandwidth, latency, etc.; device storage capacity, processing power, etc.), the presently disclosed inventive concepts include the use of an optimization model such as model 404c shown in FIG. 4.

The mathematical optimization model here gives an optimal choice of wearables given the measurements that need to be monitored. This is done putting in consideration resource restrictions such as the total budget for wearables and monitoring constraints such as the total bandwidth of the network through which measurements from all wearables are pushed, data storage capacities, data processing resource constraints, and any other such resource constraints.

According to a preferred embodiment, one may formulate the inventive optimization model as follows:

$$\text{Min} \sum_{i \in I} c_i \cdot X_i \quad (3)$$

$$\text{Subject to}: \sum_{i \in I} z_{im} \cdot X_i \geq 1, \forall\, m \in M \quad (4)$$

$$\sum_{i \in I} a_{ij} \cdot X_i \leq K_j, \forall\, j \in J \quad (5)$$

$$\sum_{i \in I} c_i \cdot X_i \leq B \quad (6)$$

$$X_i \in \{0, 1\}, \forall\, i \in I \quad (7)$$

Let I be the set of possible devices, $c_i$ be the cost of device i in set I, and B be the maximum budget for chosen devices. The set M is the set of measurements that should be monitored, e.g. as determined by the metrics identified by the classification model 404b. Input parameter $z_{im}$ is assigned a valuable of 1 if device i in set I monitors/covers measurement m in set M and zero otherwise. The set J is defined as the set of resources in the system, where $a_{ij}$ is the resource consumption of device i in set I from resource j in set J. $K_j$ is the available capacity of resource j in set J of the system.

Now, the problem becomes: which devices in the set of devices should be chosen as part of the optimal set, in order to cover all measurements in the set M, with the objective of minimizing the total costs and the constraints of making sure that all measurements are covered, all resource capacities are not exceeded, and the total cost of these chosen devices does not exceed the budget. To do so, in one embodiment the inventive concepts employ a definition $X_i$, $\forall i \in I$ as a binary variable that takes the value of 1 if device $i \in I$ is to be chosen/recommended, and zero otherwise.

In accordance with the foregoing formulation, the objective function (3) minimizes the total cost of the chosen wearables. Constraint (4) ensures that all measurements that we should be monitoring are covered by the chosen optimal set of wearables. Constraint (5) ensures that the maximum capacity of each resource is not exceeded, and constraint (6) is the budget constraint. Lastly, constraint (7) is the binary restriction on decision variables.

The output of the optimization model is preferably optimal a recommended set of devices (e.g. 406b) for the individual patient, given the metrics to be monitored and corresponding constraints. To facilitate identifying the optimum set of devices, a large corpus of healthcare solutions in IoT, device and applications (e.g. device capabilities and services 402d) is provided as an input to the optimization model, which helps construct a hash mapping table between measurements, health risks, and available solutions and resources (e.g. available resources 402c). If there is no appropriate device or IoT sensors that can help monitor a particular measurement, this can be given back as a feedback to application developers or device manufacturers to develop these on-demand non-existent technologies. Through this feedback, the device manufacturers understand the market for these devices and can target new technologies to the appropriate markets, which provides an overall added advantage for our framework.

Figure 5:
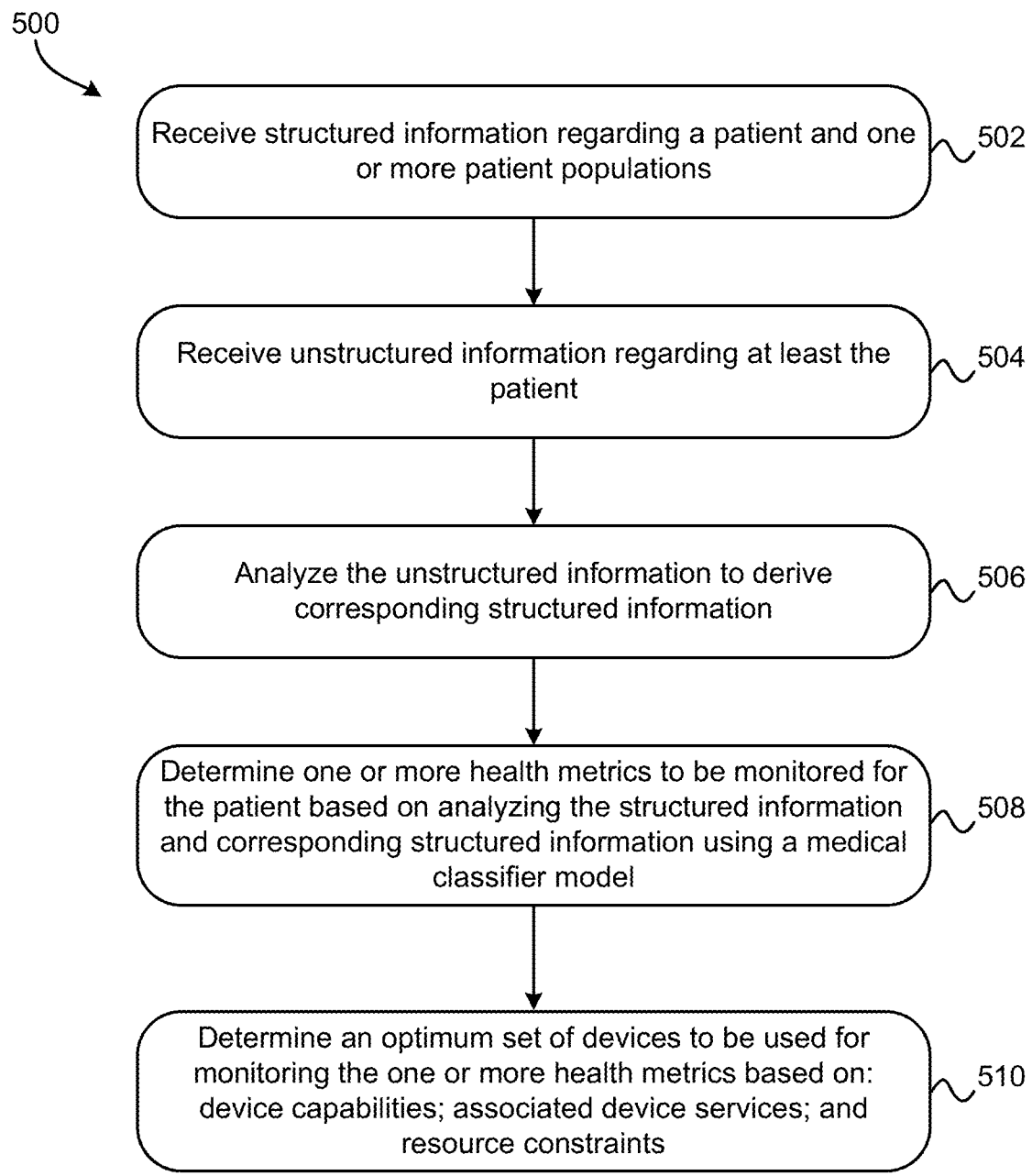
FIG. 5 illustrates a method 500 of providing personalized recommendations for monitoring and/or managing a health condition using one or more devices, in accordance with one embodiment.

Now referring to FIG. 5, a flowchart of a method 500 is shown according to one embodiment. The method 500 may be performed in accordance with the present invention in any of the environments depicted in FIGS. 1-4, among others, in various embodiments. Of course, more or less operations than those specifically described in FIG. 5 may be included in method 500, as would be understood by one of skill in the art upon reading the present descriptions.

Each of the steps of the method 500 may be performed by any suitable component of the operating environment. For example, in various embodiments, the method 500 may be partially or entirely performed by one or more servers, computers, or some other device having one or more processors therein. The processor, e.g., processing circuit(s), chip(s), and/or module(s) implemented in hardware and/or software, and preferably having at least one hardware component may be utilized in any device to perform one or more steps of the method 500. Illustrative processors include, but are not limited to, a central processing unit (CPU), an application specific integrated circuit (ASIC), a field programmable gate array (FPGA), etc., combinations thereof, or any other suitable computing device known in the art.

As shown in FIG. 5, method 500 includes operation 502, in which first structured information regarding a patient and a first set of one or more patient populations is received. The first structured information may include any suitable structured information, but preferably includes at least demographic information and/or health history information for each of the patient and the one or more patient populations. The patient populations may be defined at any suitable level of granularity and according to any suitable distinguishing characteristics, but preferably include at least a population that is medically relevant to the patient, i.e. at least includes patients having similar demographics, health history, genetic makeup, occupational history, and/or other characteristics represented by the structured information. Structured data, in one approach, may include structured data 402a as shown in FIG. 4 and may be obtained from any suitable source, including public sources for at least the one or more patient populations.

In operation 504, unstructured information regarding at least the patient, but optionally also regarding a second set of one or more patient populations, is received. As understood herein, the first and second sets of patients may overlap in whole or in part, or may be mutually exclusive, in various approaches. The unstructured information may include any combination of text, images, and/or videos relating to health status. For example, unstructured information may include electronic health records, doctor's handwritten notes, medical images such as X-ray scans or magnetic resonance imaging (MRI) scans, etc.; medical videos such as sonograms, CT scan videos, videos depicting blood flow, videos depicting a patient performing a medical evaluation, etc. as would be understood by persons having ordinary skill in the art upon reading the instant descriptions and in accordance with various embodiments of the inventive concepts presented herein. Unstructured data, in one embodiment, may include unstructured data 402b such as shown in FIG. 4 and may be obtained from any suitable source, including public sources for unstructured data regarding the patient population(s).

In operation 506, method 500 includes analyzing the unstructured information (e.g. corresponding to analysis process 404 as shown in FIG. 4) to derive second structured information. Analyzing the unstructured information in various embodiments may include any suitable form or technique of extracting information therefrom in a structured manner, i.e. "structuring" the unstructured information to derive as much relevant medical information therefrom as possible. Accordingly, in one approach analyzing the unstructured information may be considered to include building an extraction model or model(s) configured to extract specific types of structured information from particular types of unstructured information, e.g. using machine learning techniques.

The manner of analyzing the unstructured information (e.g. process 404a of FIG. 4) will depend upon the type of unstructured information. For example, where unstructured information includes textual information, a Term Frequency-Inverse Document Frequency (tf-idf) classifier may be applied to the unstructured information to derive common terms and associations therebetween within a given dataset of unstructured information. Similarly, for images and videos, any suitable image analysis/classification/data extraction technique known in the art may be employed to extract structured information therefrom.

Continuing with operation 508, health metric(s) associated with or otherwise indicative of a particular health status are determined based on analyzing the first structured information, and the second structured information derived from the unstructured information, in combination. Preferably the analysis includes historical information for the first and/or second sets of one or more patient populations so as to provide an appropriate sampling of medical information and associated metrics for monitoring. The health metrics may be determined using a classification model, such as a decision tree 300 shown in FIG. 3 or any other suitable type of classification model, e.g. model 404b as shown in FIG. 4, in various embodiments.

Regardless of the particular type of classification model, the result of the determination is a list of metrics, and optionally associated weights, to be monitored for the patient. See output 406a of FIG. 4 for a graphical example. Monitoring these health metrics will assist the patient in proactively managing health decisions so as to avoid or delay the onset of a detrimental health condition, or to accelerate achieving a particular desired medical outcome.

However, as noted above, the list of metrics to be monitored, and associated devices required to perform such monitoring, may be a practical difficulty or impossibility for some patients. Accordingly, the metrics to be monitored (along with any associated weights), a list of possible devices for monitoring such metrics, and associated capabilities, services, and practical resource constraints (technological and/or financial) are considered according to an optimization model in operation 510.

Specifically, operation 510 of method 500 includes determining an optimum set of devices (e.g. recommended list of devices 406*b*) to be used for monitoring the one or more health metrics based on: device capabilities; associated device services; and resource constraints. The optimization model may be in the form of process 406*c* as shown in FIG. 4, in one approach, or any equivalent thereof without departing from the scope of the present disclosures.

Accordingly, method 500 is directed to the general notion of taking structured and, importantly, unstructured information as input to train a classification model and subsequently evaluate patient information to determine a set of metrics to be monitored for the patient. Of course, it should be understood that method 500 in various embodiments may include any additional/alternative features described herein in any permutation, without departing from the scope of the inventive concepts presented herein.

In a particularly preferred embodiment, method 500 may include the additional notion of monitoring a patient's health metric values over time (e.g. as shown in FIG. 4 via process 404*d*), preferably in a substantially continuous manner, to detect changes that may be indicative of evolving health status or development of a new condition, and/or relief from a prior existing condition, etc. as would be understood by a person having ordinary skill in the art upon reading the present descriptions.

In a particularly preferred embodiment, therefore, method 500 may include continuously monitoring one or more health metrics of a patient using a set of optimum devices determined according to the method 500 described above. Continuous observation may include periodic, episodic, or any other type of discrete measurement, and need not be an uninterrupted set of measurements over the given observation period. Method 500 may also include comparing values of the one or more health metrics of the patient (e.g. patient metric values 406*c*) to one or more corresponding event trigger thresholds (e.g. according to process 404*e* of FIG. 4).

If the comparison yields a determination that no metric values have exceeded the predefined event trigger thresholds, then monitoring may continue as described hereinabove until such a threshold violation is determined. Notably, while the event triggers may be predetermined, e.g. based on reviewing medical literature, demographics, etc. as described hereinabove with reference to the classification model and FIG. 3, in more approaches event triggers may be adjusted dynamically, e.g. based on similar analysis of historical medical information coupled with changing conditions of the patient.

Upon determining, based on the comparison, that at least one of the one or more health metrics is characterized by a value exceeding the corresponding event trigger threshold, the method 500 may further include outputting the values 406*c* of the one or more health metrics of the patient; and combining the output values of the one or more health metrics of the patient with corresponding historical values 402*e* of the one or more health metrics of the patient collected over time to generate a comprehensive set of values of the one or more health metrics of the patient. This comprehensive, updated set of patient information is used to determine a new set of one or more health metrics 406*a* to be monitored for the patient. The determination may be based in whole or in part on analyzing the comprehensive set of values using the classification model 404*b*; and a new or updated optimum set of devices may be selected for monitoring the new set of one or more health metrics based on: device capabilities; associated device services; and resource constraints.

In accordance with the foregoing embodiment, the presently disclosed inventive concepts are advantageously capable of detecting important changes in health status based on continuous monitoring of health metrics, as well as providing real-time updates to the proper set of devices (taking into account the various constraints discussed herein) for a given patient to utilize in monitoring and managing their health.

In addition to the foregoing continuous monitoring and updating capability, method 500 may include additional and/or alternative features and/or operations such as analyzing the unstructured information in operation 506 comprising building at least one extraction model. The extraction model is preferably configured to extract structured information from the unstructured information using at least one machine learning technique. For example, if the unstructured information includes textual information, Text Frequency-Inverse Document Frequency (tf-idf) or other equivalent textual analysis techniques may be applied. If the unstructured information includes image and/or video data, suitable image processing algorithms such as support vector machine (SVM) techniques, maximum entropy discrimination (MED) techniques, or any other suitable techniques appreciable by a skilled artisan upon reading these descriptions may be employed without departing from the scope of the inventive concepts presented herein.

In still more embodiments, method 500 may include determining one or more weights associated with each of the one or more health metrics, e.g. using the classification model. Preferably, the weights are indicative of relative importance of a given metric in predicting a future health status of the patient. For instance, in one approach metrics may be assigned weights computed based on an aggregation of one or more of: weights of a particular metric that triggered an event (e.g. in response to continuous monitoring of the metric over time to detect an anticipated/possible future medical development); weights of metrics associated with the particular metric that triggered the event, and any relevant correlation coefficients between the two. Assignment of weights may extend monitoring to new metrics over time, e.g. as a health condition progresses and/or secondary health conditions become relevant. Assignment of weights may also or alternatively cause a particular metric to cease being monitored, e.g. if no longer relevant to a particular health condition for a given patient.

In another approach, if a particular value-related event does not extend the monitoring to any new metrics, weights of the existing metric(s) that triggered the event may be computed as a non-decreasing function of an absolute difference between one or more monitored metric values and a predefined threshold value (or threshold difference) that triggered the value-related event.

As suggested hereinabove, method 500 may include training the classification model using a training set comprising historical medical information for the one or more patient populations, the historical medical information most preferably comprising structured and unstructured information.

The determination of optimal device set(s) according to method 500 may involve an optimization model comprising a plurality of rules configured to minimize financial cost of the optimum set of devices while ensuring the optimum set of devices: includes all device capabilities necessary to monitor the one or more health metrics; and will not exceed any applicable technological constraints of: any respective one of the optimum set of devices; and an operating environment in which the one or more health metrics are to be measured. Accordingly, the presently disclosed inventive concepts, particularly via the optimization model, represent an improvement to computer technology in the form of a set of objective rules (essentially mathematical relationships) that enable computers to perform a function traditionally reserved for humans (medical professionals in particular) and performed according to subjective considerations.

Here, a computer can take into account the various constraints and capabilities of a vast number of available candidate devices and the potential need to evaluate a diverse array of health metrics, while also considering the financial and technological constraints of the patient and devices/operating environment, respectively. The computer may evaluate these criteria according to the aforementioned objective rules, and provide an improved recommendation to a patient relative to a human doctor that is not capable or does not have sufficient time and expertise to evaluate all these considerations.

Thus, using the presently disclosed inventive techniques conveys an improvement to computer technology in the form of enabling computers to perform a function previously only capable of being performed by humans, and in a manner that uses objective rules rather than subjective criteria. This implementation yields improved quality of results and corresponding health care for the patient, representing an improvement to another field (i.e. medicine, and preventative medicine in particular).

In a particularly preferred embodiment, the rules include: an objective function $\Sigma_{i \in I} c_i \cdot X_i$ configured to minimize a total cost of the optimum set of devices, wherein the cost is defined by a plurality of constraints. The constraints include, but are not limited to: a capability constraint $\Sigma_{i \in I} z_{im} \cdot X_i \geq 1$, $\forall m \in M$ configured to ensure the optimum set of devices includes all device capabilities necessary to monitor the one or more health metrics; a resource constraint $\Sigma_{i \in I} a_{ij} \cdot X_i \leq K_j$, $\forall \in J$ configured to ensure the optimum set of devices will not exceed any applicable technological constraints of individual ones of the optimum set of devices and an operating environment in which the one or more health metrics are to be measured; and a financial constraint $\Sigma_{i \in I} c_i \cdot X_i \leq B$ configured to ensure a financial total cost of the optimum set of devices does not exceed a predetermined budget.

In accordance with the foregoing formulation, I is a set of possible devices to be included in the optimum set of devices; $c_i$ is the cost of a given device $i \in I$, B is a maximum budget for the optimum set of devices; M is a set of measurements necessary to monitor the one or more health metrics; $z_{im}$ is a binary input parameter having a value of 1 if wearable $i \in I$ is capable of collecting measurement $m \in M$, and zero otherwise; $X_i$ is a binary variable having a value of 1 if a given device $i \in I$ is to be recommended/used, and a value of zero otherwise; J is a set of resources available to the optimum set of devices in the operating environment in which the one or more health metrics are to be monitored; $a_{ij}$ is a resource consumption of a given device $i \in I$; and $K_j$ is an available capacity of resource $j \in J$.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A computer-implemented method for providing personalized recommendations of devices for monitoring and/or managing a health condition, the method comprising:
    receiving, at a computer, first structured information regarding a patient and a first set of one or more patient populations;
    receiving, at the computer, unstructured information regarding at least the patient and a second set of one or more patient populations, wherein the unstructured information comprises an electronic health record or portion(s) thereof;
    analyzing, using the computer, the unstructured information to derive second structured information;
    training a classification model using a training set comprising historical medical information for either or both of: the first set of one or more patient populations; and the second set of one or more patient populations, wherein the historical medical information comprises structured information and unstructured information, and wherein the classification model comprises a decision tree algorithm;
    determining, using the computer, one or more health metrics to be monitored for the patient based on analyzing each of the first structured information and the second structured information using the classification model; and
    determining, using the computer, an optimum set of devices to be used for monitoring the one or more health metrics;
    wherein determining the optimum set of devices utilizes an optimization model comprising a plurality of rules configured to minimize a financial cost of the optimum set of devices while ensuring the optimum set of devices:
        includes all device capabilities necessary to monitor the one or more health metrics; and
        will not exceed applicable technological constraints of:
            any respective one of the optimum set of devices; and
            an operating environment in which the one or more health metrics are to be measured; and
    wherein the rules comprise:
    an objective function $\Sigma_{i \in I} c_i \cdot X_i$ configured to minimize a total cost of the optimum set of devices, wherein the total cost is defined by a plurality of constraints, comprising:
        a capability constraint $\Sigma_{i \in I} z_{im} \cdot X_i \geq 1$, $\forall m \in M$ configured to ensure the optimum set of devices includes all device capabilities necessary to monitor the one or more health metrics;
        a resource constraint $\Sigma_{i \in I} a_{ij} \cdot X_i \leq K_j$, $\forall j \in J$ configured to ensure the optimum set of devices will not exceed any of the applicable technological constraints of:
            individual ones of the optimum set of devices; and
            the operating environment in which the one or more health metrics are to be measured; and
        a financial constraint $\Sigma_{i \in I} c_i \cdot X_i \leq B$ configured to ensure the financial cost of the optimum set of devices does not exceed a predetermined budget; and wherein:
I is a set of possible devices to be included in the optimum set of devices;
$c_i$ is the financial cost of a given device $i \in I$;
B is a maximum budget for the optimum set of devices;
M is a set of measurements necessary to monitor the one or more health metrics;
$z_{im}$ is a binary input parameter having a value of 1 if the given device $i \in I$ is capable of collecting measurement $m \in M$, and zero otherwise;
$X_i \forall i \in I$ is a binary variable having a value of 1 if the given device $i \in I$ is one of the optimum set of devices recommended for monitoring and/or managing the health condition, and zero otherwise;
J is a set of resources available to the optimum set of devices in the operating environment in which the one or more health metrics are to be monitored;
$a_{ij}$ is a resource consumption of a given device $i \in I$; and
$K_j$ is an available capacity of resource $j \in J$.

2. The method as recited in claim 1, wherein analyzing the unstructured information comprises building at least one extraction model configured to extract structured information from the unstructured information using a machine learning technique.

3. The method as recited in claim 1, wherein the classification model also determines one or more weights associated with each of the one or more health metrics, the weights being indicative of relative importance of a given metric in predicting a future health status of the patient.

4. The method as recited in claim 1, comprising building the decision tree algorithm, wherein building the decision tree algorithm comprises partitioning a decision tree model using one or more attributes based at least in part on: an entropy associated with the one or more attributes.

5. The method as recited in claim 1, wherein the optimum set of devices is determined based on: device capabilities; associated device services; and resource constraints; and
wherein the resource constraints comprise financial constraints of the patient and technological constraints selected from the group consisting of: the device and an operating environment in which the health metrics are to be monitored for the patient.

6. The method as recited in claim 1, comprising:
comparing values of the one or more health metrics of the patient to one or more corresponding event trigger thresholds;
upon determining, based on the comparison, that at least one of the one or more health metrics is characterized by a value exceeding the corresponding event trigger threshold, outputting the values of the one or more health metrics of the patient;
combining the values of the one or more health metrics of the patient with corresponding historical values of the one or more health metrics of the patient collected over time to generate a comprehensive set of values of the one or more health metrics of the patient;
determining a new set of one or more health metrics to be monitored for the patient based on analyzing the comprehensive set of values using the classification model; and
determining a new optimum set of devices to be used for monitoring the new set of one or more health metrics based on: device capabilities; associated device services; and resource constraints.

7. The method as recited in claim 1, comprising assigning a plurality of labels to demographic data using a trained machine learning algorithm.

8. The method as recited in claim 7, wherein the trained machine learning algorithm comprises a decision tree algorithm;
wherein the decision tree algorithm is characterized by including a root node and a plurality of leaf nodes; and
wherein each leaf node independently represents a set K of one or more most likely health condition(s) for patient(s) exhibiting a combination of demographics represented by a path from the root node to one of the leaf node(s).

9. The method as recited in claim 1, wherein the decision tree algorithm is characterized by including a root node and a plurality of leaf nodes;
wherein each leaf node independently represents a set K of one or more most likely health condition(s) for patient(s) exhibiting a combination of demographics represented by a path from the root node to the leaf node; and
wherein the root node represents a demographic attribute associated with a particular health condition.

10. A computer program product for providing personalized recommendations of devices for monitoring and/or managing a health condition, the computer program product comprising a computer readable storage medium having program instructions embodied therewith, wherein the computer readable storage medium is not a transitory signal per se, the program instructions executable by a processor to cause the processor to perform a method comprising:
receiving, at the processor, first structured information regarding a patient and a first set of one or more patient populations;
receiving, at the processor, unstructured information regarding at least the patient and a second set of one or more patient populations wherein the unstructured information comprises an electronic health record or portion(s) thereof;
analyzing the unstructured information to derive second structured information;
training a classification model using a training set comprising historical medical information for either or both of: the first set of one or more patient populations; and the second set of one or more patient populations, wherein the historical medical information comprises structured information and unstructured information, and wherein the classification model comprises a decision tree algorithm;
determining, by the processor, one or more health metrics to be monitored for the patient based on analyzing the first structured information and the second structured information using the classification model; and
determining, by the processor, an optimum set of devices to be used for monitoring the one or more health metrics;
wherein determining the optimum set of devices utilizes an optimization model comprising a plurality of rules configured to minimize a financial cost of the optimum set of devices while ensuring the optimum set of devices:
includes all device capabilities necessary to monitor the one or more health metrics; and
will not exceed any applicable technological constraints of:
individual ones of the optimum set of devices; and
an operating environment in which the one or more health metrics are to be measured; and wherein the rules comprise:
an objective function $\Sigma_{i \in I} c_i \cdot X_i$ configured to minimize a total cost of the optimum set of devices, wherein the total cost is defined by a plurality of constraints, comprising:
  a capability constraint $\Sigma_{i \in I} z_{im} \cdot X_i \geq 1$, $\forall m \in M$ configured to ensure the optimum set of devices includes all device capabilities necessary to monitor the one or more health metrics;
  a resource constraint $\Sigma_{i \in I} a_{ij} \cdot X_i \leq K_j$, $\forall \in J$ configured to ensure the optimum set of devices will not exceed any of the applicable technological constraints of:
    the individual ones of the optimum set of devices; and
    the operating environment in which the one or more health metrics are to be measured; and
  a financial constraint $\Sigma_{i \in I} c_i \cdot X_i \leq B$ configured to ensure the financial cost of the optimum set of devices does not exceed a predetermined budget; and
wherein:
  I is a set of possible devices to be included in the optimum set of devices;
  $c_i$ is the financial cost of a given device $i \in I$,
  B is a maximum budget for the optimum set of devices;
  M is a set of measurements necessary to monitor the one or more health metrics,
  $z_{im}$ is a binary input parameter having a value of 1 if wearable $i \in I$ is capable of collecting measurement $m \in M$, and zero otherwise;
  $X_i \forall i \in I$ is a binary variable having a value of 1 if the given device $i \in I$ is one of the optimum set of devices recommended for monitoring and/or managing the health condition, and zero otherwise;
  J is a set of resources available to the optimum set of devices in the operating environment in which the one or more health metrics are to be monitored;
  $a_{ij}$ is a resource consumption of a given device $i \in I$; and
  $K_j$ is an available capacity of resource $j \in J$.

11. The computer program product as recited in claim 10, comprising building the decision tree algorithm, wherein building the decision tree algorithm comprises partitioning a decision tree model using one or more attributes based at least in part on: an entropy associated with the one or more attributes.

12. The computer program product as recited in claim 10, wherein the classification model also determines one or more weights associated with each of the one or more health metrics, the weights being indicative of relative importance of a given metric in predicting a future health status of the patient.

13. The computer program product as recited in claim 10, comprising generating a vector representing one or more probable causes of one or more health conditions based at least in part on the decision tree algorithm.

14. The computer program product as recited in claim 10, wherein the optimum set of devices is determined based on: device capabilities; associated device services; and resource constraints; and
wherein the resource constraints comprise financial constraints of the patient and technological constraints selected from the group consisting of: the device and an operating environment in which the health metrics are to be monitored for the patient.

15. The computer program product as recited in claim 10, comprising:
comparing values of the one or more health metrics of the patient to one or more corresponding event trigger thresholds;
upon determining, based on the comparison, that at least one of the one or more health metrics is characterized by a value exceeding the corresponding event trigger threshold, outputting the values of the one or more health metrics of the patient;
combining the values of the one or more health metrics of the patient with corresponding historical values of the one or more health metrics of the patient collected over time to generate a comprehensive set of values of the one or more health metrics of the patient;
determining a new set of one or more health metrics to be monitored for the patient based on analyzing the comprehensive set of values using the classification model; and
determining a new optimum set of devices to be used for monitoring the new set of one or more health metrics.

16. A computer-implemented method for providing personalized recommendations of devices for monitoring and/or managing a health condition, the method comprising:
receiving, at a computer, first structured information regarding a patient and a first set of one or more patient populations;
receiving, at the computer, unstructured information regarding at least the patient and a second set of one or more patient populations, wherein the unstructured information comprises an electronic health record or portion(s) thereof;
analyzing, using the computer, the unstructured information to derive second structured information;
training a classification model using a training set comprising historical medical information for either or both of: the first set of one or more patient populations; and the second set of one or more patient populations, wherein the historical medical information comprises structured information and unstructured information, and wherein the classification model comprises a decision tree algorithm;
determining, using the computer, one or more health metrics to be monitored for the patient based on analyzing each of the first structured information and the second structured information using the classification model; and
determining, using the computer, an optimum set of devices to be used for monitoring the one or more health metrics;
assigning a plurality of labels to demographic data using a trained machine learning algorithm;
generating a vector representing one or more probable causes of one or more health conditions based at least in part on the decision tree algorithm;
building the decision tree algorithm, wherein building the decision tree algorithm comprises partitioning a decision tree model using one or more attributes based at least in part on: an entropy associated with the one or more attributes; and/or an information gain associated with the one or more attributes;
wherein determining the optimum set of devices utilizes an optimization model comprising a plurality of rules configured to minimize financial cost of the optimum set of devices while ensuring the optimum set of devices:

includes all device capabilities necessary to monitor the one or more health metrics; and will not exceed applicable technological constraints of:
any respective one of the optimum set of devices; and
an operating environment in which the one or more health metrics are to be measured; and wherein the rules comprise an objective function $\Sigma_{i \in I} c_i \cdot X_i$ configured to minimize a total cost of the optimum set of devices, wherein the total cost is defined by a plurality of constraints, comprising:

a capability constraint $\Sigma_{i \in I} z_{im} \cdot X_i \geq 1$, $\forall m \in M$ configured to ensure the optimum set of devices includes all device capabilities necessary to monitor the one or more health metrics;

a resource constraint $\Sigma_{i \in I} a_{ij} \cdot X_i \leq K_j$, $\forall \in J$ configured to ensure the optimum set of devices will not exceed any of the applicable technological constraints of:
individual ones of the optimum set of devices; and
the operating environment in which the one or more health metrics are to be measured; and a financial constraint $\Sigma_{i \in I} c_i \cdot X_i \leq B$ configured to ensure the financial cost of the optimum set of devices does not exceed a predetermined budget; and wherein:
I is a set of possible devices to be included in the optimum set of devices;

$c_i$ is the financial cost of a given device $i \in I$;

B is a maximum budget for the optimum set of devices;

M is a set of measurements necessary to monitor the one or more health metrics;

$z_{im}$ is a binary input parameter having a value of 1 if the given device $i \in I$ is capable of collecting measurement $m \in M$, and zero otherwise;

$X_i \forall i \in I$ is a binary variable having a value of 1 if the given device $i \in I$ is one of the optimum set of devices recommended for monitoring and/or managing the health condition, and zero otherwise;

J is a set of resources available to the optimum set of devices in the operating environment in which the one or more health metrics are to be monitored;

$a_{ij}$ is a resource consumption of a given device $i \in I$; and $K_j$ is an available capacity of resource $j \in J$; and wherein the trained machine learning algorithm comprises a decision tree algorithm;

wherein the decision tree algorithm is characterized by including a root node and a plurality of leaf nodes;

wherein each leaf node independently represents a set K of one or more most likely health condition(s) for patient(s) exhibiting a combination of demographics represented by a path from the root node to the leaf node;

wherein the root node represents a demographic attribute associated with a particular health condition;

wherein the unstructured information comprises information selected from the group consisting of: images, audio, and videos;

wherein analyzing the unstructured information comprises building at least one extraction model configured to extract structured information from the unstructured information;

wherein the classification model also determines one or more weights associated with each of the one or more health metrics, the weights being indicative of relative importance of a given metric in predicting a future health status of the patient;

wherein the optimum set of devices is determined based on: device capabilities, associated device services, and resource constraints; and wherein the resource constraints comprise financial constraints of the patient and technological constraints selected from the group consisting of: the device and an operating environment in which the health metrics are to be monitored for the patient.

* * * * *